United States Patent
Leinvuo et al.

(10) Patent No.: US 6,842,258 B1
(45) Date of Patent: Jan. 11, 2005

(54) METHOD OF MEASURING THE GEOMETRY OF GROOVES IN AN ELONGATED ELEMENT

(75) Inventors: Joni Leinvuo, Helsinki (FI); Jouko Viitanen, Tampere (FI); Juha Korpinen, Nokia (FI); Jani Uusitalo, Tampere (FI)

(73) Assignee: Nextrom Holdings S.A., Morges (CH)

( * ) Notice: Subject to any disclaimer, the term of this patent is extended or adjusted under 35 U.S.C. 154(b) by 346 days.

(21) Appl. No.: 10/049,104
(22) PCT Filed: Sep. 27, 2000
(86) PCT No.: PCT/FI00/00826
§ 371 (c)(1), (2), (4) Date: Feb. 27, 2002
(87) PCT Pub. No.: WO01/23872
PCT Pub. Date: Apr. 5, 2001

(30) Foreign Application Priority Data

Sep. 29, 1999 (FI) .............................................. 19992088

(51) Int. Cl.$^7$ ............................................... G01B 11/24
(52) U.S. Cl. ..................... 356/601; 356/238.2; 356/430
(58) Field of Search ............................... 356/601–613, 356/238.2, 429–431, 73.1

(56) References Cited

U.S. PATENT DOCUMENTS

| 4,358,202 A | 11/1982 | Puffer et al. |
| 4,551,020 A | * 11/1985 | Reid et al. .................. 356/73.1 |
| 4,705,957 A | 11/1987 | Puffer et al. |

FOREIGN PATENT DOCUMENTS

| DE | 40 24 546 C1 | 11/1991 |
| DE | 44 11 986 A1 | 10/1995 |
| JP | A 4-52503 | 2/1992 |
| WO | WO 89/05468 | 6/1989 |
| WO | WO 93/03349 | 2/1993 |
| WO | WO 93/03350 | 2/1993 |

* cited by examiner

Primary Examiner—Richard A. Rosenberger
Assistant Examiner—Vincent P. Barth
(74) Attorney, Agent, or Firm—Oliff & Berridge, PLC

(57) ABSTRACT

The invention relates to a method and an arrangement for measuring the geometry of grooves in an elongated element, which grooves (2) extend as continuous grooves over the whole length of the elongated element (1), circling around the element, in which method the surface of the elongated element is scanned by of a camera (6). In order to achieve simple non-contact measurement, the elongated element (1) is arranged to travel at the vertex through an annular biconical minor or through a biconical bevelled mirror (3) comprising several plane mirrors, and through a plane mirror structure (4) arranged at an oblique angle relative to the direction of travel of the elongated element (1). An annular laser beam is directed to the plane mirror structure in such a way that the plane mirror structure (4) reflects the beam onto the surface of the elongated element (1) through the outer surface (3a) of the biconical mirror or bevelled cone mirror. The image of the surface profile of the elongated element (1) produced from the surface of the elongated element (1) by means of the inner surface (3b) of the biconical mirror or bevelled cone mirror (3) is turned to one side by means of the plane mirror structure (4) to allow the study of the groove geometry.

6 Claims, 1 Drawing Sheet

METHOD OF MEASURING THE GEOMETRY OF GROOVES IN AN ELONGATED ELEMENT

Figure 1:
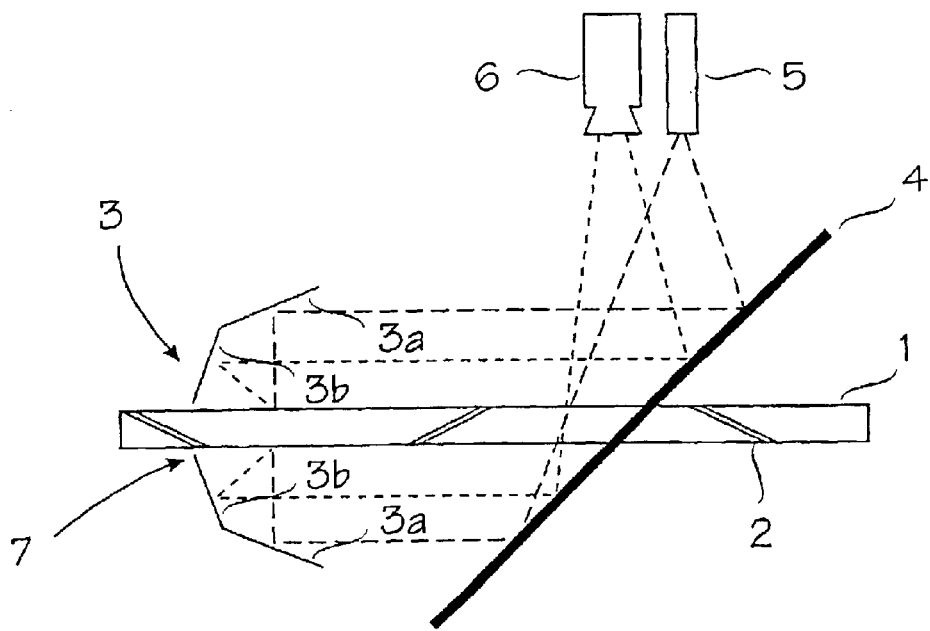

The invention relates to a method of measuring the geometry of grooves in an elongated element, which grooves extend as continuous grooves over the whole length of the elongated element, circling around the element, in which method the surface of the elongated element is scanned by means of a camera. The invention also relates to an arrangement for measuring the geometry of grooves in an elongated element.

Measurement of the geometry of grooves in an elongated element relates to the manufacture of cables, for example, a more detailed example being the manufacture of the central element, i.e. a slotted core element, of a fibre cable, which is technically relatively difficult The problem is that the walls forming the sides of the grooves in the element easily decline into an incorrect position, whereby the central element cannot be used as intended. As regards the manufacture of the cable, it is important that the grooves of the central element have the right geometry; thus, the measurement of the groove geometry is essential.

Measuring the geometry of grooves has been difficult and laborious. In the field, solutions based on a mechanical follower have been used for measuring the groove geometry. As for the maintenance, however, such mechanical solutions are difficult and laborious. Further, there is always the risk that the element to be measured is damaged by the mechanical contact.

Due to the above drawbacks, non-contact solutions have been provided in the field. An example of the non-contact solutions in the field is the method and equipment disclosed in German Offenlegungsschrift 44 11 986. The solution is based on the use of four cameras. Complexity and consequently also the high costs are drawbacks of the solution. Moreover, due to the complexity, the usability of the solution is not the best possible.

Another example of the non-contact solutions known in the field is the solution disclosed in Japanese publication 04052503 A (Japanese patent application 02161899). The solution according to the Japanese publication utilizes one camera arranged to rotate around the element to be measured. Complexity and a slow measuring rate are drawbacks of the solution. The measuring rate is slow, because, for example, the camera has to be rotated around the element to be measured.

An object of the invention is to provide a method and an arrangement, by means of which the drawbacks of the prior art can be eliminated. This is achieved by means of the method and the arrangement according to the invention. The method according to the invention is characterized by arranging an elongated element to travel at the vertex through an annular biconical mirror or through a biconical bevelled mirror comprising several plane mirrors, and through a plane mirror structure arranged at an oblique angle relative to the direction of travel of the elongated element; directing an annular laser beam to the plane mirror structure in such a way that the plane mirror structure reflects the beam onto the surface of the elongated element through the outer surface of the biconical mirror or bevelled cone mirror, and turning the image of the surface profile of the elongated element produced from the surface of the elongated element by means of the inner surface of the biconical mirror or bevelled cone mirror to one side by means of the plane mirror structure to allow the study of the groove geometry. The arrangement according to the invention, in turn, is characterized by comprising an annular biconical mirror or a bevelled cone mirror comprising several plane mirrors, at the vertex of which there is an opening, through which the elongated element is arranged to travel; a plane mirror structure arranged at an oblique angle relative to the direction of travel of the elongated element, through which structure the elongated element is arranged to travel; and a laser light source arranged to direct an annular laser beam to the plane mirror structure in such a way that the plane mirror structure reflects the beam onto the surface of the elongated element through the outer surface of the biconical mirror or bevelled cone mirror; and by arranging the image of the surface profile of the elongated element produced from the surface of the elongated element by means of the inner surface of the biconical mirror or bevelled cone mirror in such a way that it can be turned to one side by means of the plane mirror structure to allow the study of the groove geometry.

An advantage of the invention is, above all, that it allows non-contact measurement of the geometry of all the grooves in the element simultaneously in a very simple manner compared with the prior art. Further, the operating principle of the invention does not impose any restrictions on the position of the groove element. Another advantage of the invention is that It allows minimization of the measuring data, which further allows quick data processing and reduces at the same time the equipment costs. Still another advantage of the invention is that it can be utilized in different applications.

Figure 2:
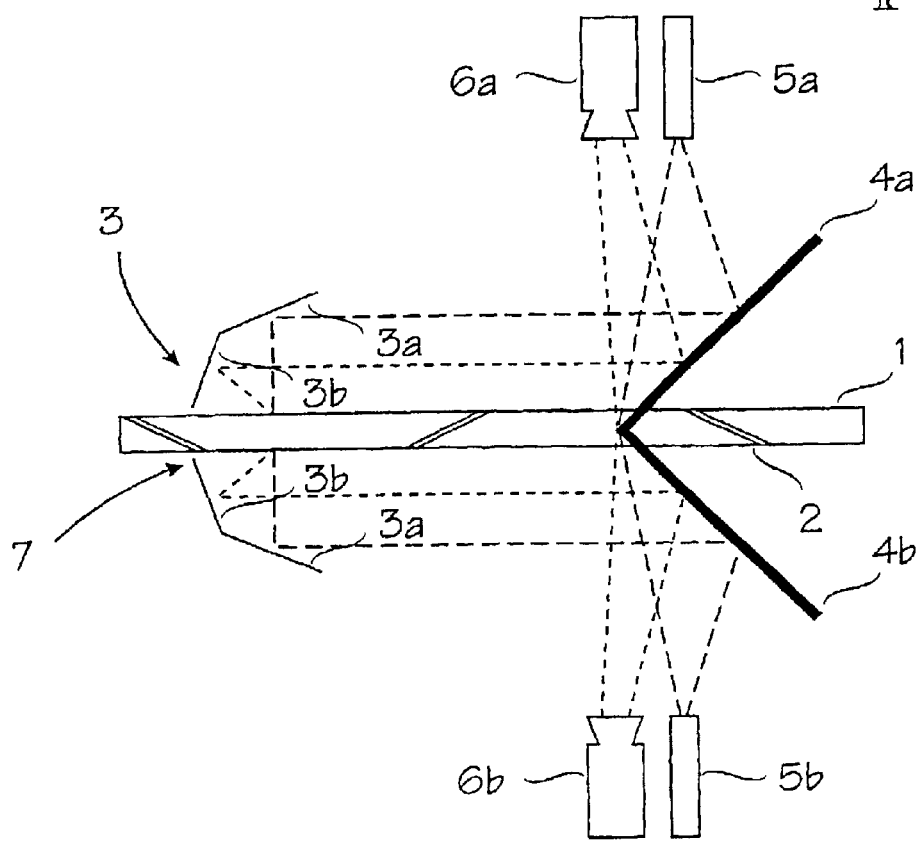

The invention will now be described in more detail, with reference to the application example illustrated by the attached drawings, of which FIG. 1 schematically shows the basic principle of a solution according to the invention as a side view; and FIG. 2 schematically shows a second embodiment of the basic principle of FIG. 1 as a side view.

FIG. 1 is a schematic side view of the basic idea of the invention. Reference numeral 1 denotes an elongated object, which may be for example the central element of a fibre cable, i.e. the central element of a slotted core cable. The surface of the elongated element 1 is provided with several grooves, which extend over the whole length of the element and circle around the element in a desired way. The grooves may circle in the same direction all the time, or alternatively change their direction of circling. FIG. 1 illustrates, by way of example, only one groove 2, but in reality there are several grooves. The structure of the elongated element as such is known to a person skilled in the art and is therefore not described in more detail herein. In this connection, it is only noted that the geometry of the grooves has to be as desired in order to enable arrangement of connector elements, such as fibres and fibre bundles into the grooves without problems.

Reference numeral 3 in FIG. 1 denotes an annular biconical mirror or a biconical bevelled mirror comprising several plane mirrors. The term 'biconical' means that the mirror surface is formed by two substantially conical mirror surfaces having a difference of angle. This is clearly shown in FIG. 1. The mirror surfaces may be formed by annular conical surfaces or bevelled cone surfaces comprising several plane mirrors. Reference numeral 4 in FIG. 1 denotes a plane mirror structure. Reference numeral 5 in FIG. 1 refers to a laser light source and reference numeral 6 to a camera.

At the vertex of the biconical mirror or bevelled cone mirror 3, there is an opening 7, through which the elongated element is arranged to travel. The elongated element 1 is also arranged to travel through the plane mirror structure 4. The plane mirror structure is arranged at an oblique angle relative to the direction of travel of the elongated element 1. The direction of travel of the elongated element is parallel to the symmetry axis of the elongated element.

In accordance with the essential idea of the invention, an annular laser beam is directed by means of the laser light source 5 to the surface of the elongated element 1 through the plane mirror 4 and the outer conical surface or bevelled surface 3a of the biconical mirror or biconical bevelled mirror 3, whereby the light illuminates the grooves 2 on the surface of the elongated element 1. A bevelled surface comprising several plane mirrors is used instead of an annular conical surface when also the corners of the grooves 2 are to be illuminated by the light. The camera 6 is directed to the inner conical surface or bevelled surface 3b of the mirror 3 through the plane mirror 4, whereby said surface reflects the image of the surface profile of the elongated element 1 generated by the laser light. The geometry of all grooves can be read from the image simultaneously. As can be seen from FIG. 1, the scanning takes place axially relative to the elongated element 1. As positioning the camera 6 on the symmetry axis of the elongated element 1 is impossible, the image of the surface profile of the elongated element 1 is turned to one side by means of the plane mirror structure 4.

The plane mirror structure 4 in the example of FIG. 1 is formed by one plane mirror. The drawback of a structure formed by one plane mirror is that, due to the elongated element 1, the whole surrounding surface cannot be seen in the image formed in the above manner. However, the measuring data may be interpolated with sufficient accuracy, so that this is not a problem in practice.

The above drawback may, however, be eliminated by using a plane mirror structure formed by two plane mirrors 4a, 4b. The principle of such a solution is shown in FIG. 2. The solution of FIG. 2 substantially corresponds to the basic principle of FIG. 1, and the corresponding parts in FIG. 2 are denoted by the same reference numerals as in FIG. 1. The essential idea of the application in FIG. 2 is that two laser light sources 5a, 5b and two cameras 6a, 6b are used. Both combinations of laser light source and camera cover at least 180 degrees of the surface of the elongated element 1, so that there are no shadowy parts. The mirror surfaces 3a and 3b are formed in the manner described in connection with FIG. 1.

The above application examples are by no means intended to limit the invention, but the invention may be modified totally freely within the scope of the claims. While the invention has here been described in connection with the central element of a slotted core cable structure, it is obvious that the invention is not limited to this aspect but may be used for measuring the geometry of grooves in any elongated element. The Invention may also be used for measuring the pitch of stranded cables and measuring the diameter in relation to all axles, for example. Further, the arrangement of the invention does not have to be precisely as shown in the figures but other solutions are also feasibly.

What is claimed is:

1. A method of measuring the geometry of grooves in an elongated element, which grooves extend as continuous grooves over the whole length of the elongated element, circling around the element, in which method a surface of the elongated element is scanned by means of a camera, comprising:

arranging the elongated element to travel through an opening at a vertex of an annular conical mirror, and through a plane mirror structure arranged at an oblique angle relative to the direction of travel of the elongated element;

directing an annular light beam to the plane mirror structure;

reflecting the light beam from the plane mirror structure onto a surface of the elongated element through an outer surface of the conical mirror;

reflecting an image of a surface profile of the elongated element, produced from the surface of the elongated element by means of the conical mirror, into the camera by means of the plane mirror structure;

forming the conical mirror from a biconical mirror or a biconical bevelled mirror including several plane mirrors; and arranging the image of the surface profile of the elongated element, to allow the study of the groove geometry, by means of the an inner surface of the biconical mirror or the biconical bevelled mirror.

2. A method according to claim 1, wherein studying the image is by means of the camera.

3. A method according to claim 1, wherein the light beam is a laser beam.

4. An arrangement for measuring the geometry of grooves in an elongated element, which grooves extend as continuous grooves over the whole length of the elongated element, circling around the element, in which arrangement the surface of the elongated element is arranged to be scanned by means of a camera, comprising:

an annular conical mirror, at a vertex of which there is an opening, through which the elongated element is arranged to travel;

a plane mirror structure arranged at an oblique angle relative to the direction of travel of the elongated element, through which structure the elongated element is arranged to travel; and a light source arranged to direct an annular light beam to the plane mirror structure in such a way that the plane mirror structure reflects the light beam onto a surface of the elongated element by means of the conical mirror, an image of a surface profile of the elongated element produced from the surface of the elongated element by means of the conical mirror is reflected into the camera by means of the plane mirror structure, the conical mirror is a biconical mirror or a biconical bevelled mirror including several plane mirrors, the plane mirror structure is arranged to reflect the light beam through an outer surface of the biconical mirror or the biconical bevelled mirror, and the image of the surface profile of the elongated element is arranged, to allow the study of the groove geometry, by means of the inner surface of the biconical mirror or bevelled cone mirror.

5. An arrangement according to claim 4, wherein the image is arranged to be studied by means of the camera.

6. An arrangement according to claim 4, wherein that the light beam is a laser beam.

* * * * *